US008017356B2

(12) United States Patent
Shimada et al.

(10) Patent No.: US 8,017,356 B2
(45) Date of Patent: Sep. 13, 2011

(54) ENDORIBONUCLEASE

(75) Inventors: Masamitsu Shimada, Otsu (JP); Masanori Takayama, Otsu (JP); Kiyozo Asada, Otsu (JP); Ikunoshin Kato, Otsu (JP)

(73) Assignee: Takara Bio Inc., Shiga (JP)

( * ) Notice: Subject to any disclaimer, the term of this patent is extended or adjusted under 35 U.S.C. 154(b) by 625 days.

(21) Appl. No.: 11/997,119

(22) PCT Filed: Jul. 4, 2006

(86) PCT No.: PCT/JP2006/313272
§ 371 (c)(1),
(2), (4) Date: Jan. 28, 2008

(87) PCT Pub. No.: WO2007/013265
PCT Pub. Date: Feb. 1, 2007

(65) Prior Publication Data
US 2010/0093026 A1 Apr. 15, 2010

(30) Foreign Application Priority Data

Jul. 26, 2005 (JP) ................... 2005-215672

(51) Int. Cl.
*C12P 19/34* (2006.01)
*C12N 9/22* (2006.01)
(52) U.S. Cl. ..................... 435/91.1; 435/199
(58) Field of Classification Search .......... None
See application file for complete search history.

(56) References Cited

FOREIGN PATENT DOCUMENTS
EP 1921136 A1 5/2008
WO 2004/113498 A2 12/2004

OTHER PUBLICATIONS

Chica et al. Curr Opin Biotechnol. Aug. 2005;16(4):378-84.*
Witkowski et al. Biochemistry. Sep. 7, 1999; 38(36): 11643-50.*
Seffernick et al. J Bacteriol. Apr. 2001; 183 (8): 2405-10.*
Database UNIPROT, "Genome sequence of the radioresistant bacterium *Deinoooocus radiodurans* R1,"Science, 1999, database accession No. Q9RWK4.
M. Holden et al., Database Uniprot [Online], XP-002513386, "Complete genomes of two clinical *Staphylococcus aureus* strains: evidence for the rapid evolution of virulence and drug resistance", EBI Accession No. Q6G7P1, Jul. 18, 2004.
O. White et al., "Genome Sequence of the Radioresistant Bacterium *Deinococcus radiodurans* R1", Science, vol. 286, pp. 1571-1577, Nov. 19, 1999.
M. Holden et al., "Complete genomes of two clinical *Staphylococcus aureus* strains: Evidence for the rapid evolution of virulence and drug resistance" PNAS, vol. 101, No. 26, pp. 9786-9791, Jun. 29, 2004.
V. Anantharaman et al., "New connections in the prokaryotic toxin-antitoxin network: relationship with the eukaryotic nonsense-mediated RNA decay system", Genome Biology (2003) 4:(12), Article R81.1-R81.15.

S. K. Christensen et al., "Overproduction of the Lon protease triggers inhibition of translation in *Escherichia coli*: involvement of the yefM-yoeB toxin-antitoxin system", Molecular Microbiology (2004) 51:(6), 1705-1717.
S. K. Christensen et al., "RelE toxins from Bacteria and *Archaea* cleave mRNAs on translating ribosomes, which are rescued by tmRNA", Molecular Microbiology (2003) 48(5), 1389-1400.
S. K. Christensen et al., "Toxin-antitoxin Loci as Stress-response-elements: ChpAK/MazF and ChpBK Cleave Translated RNAs and are Counteracted by tmRNA", J. Mol. Biol. (2003) 332, 809-819.
F. Hayes, "Toxins-Antitoxins: Plasmid Maintenance, Programmed Cell Death, and Cell Cycle Arrest", Science (2003), 301: 1496-1499.
K. Gerdes, "Toxins-Antitoxin Modules May Regulate Synthesis of Macromolecules during Nutritional Stress", J. of Bacteriology (2000), 182(3): 561-572.
G. Mittenhuber, "Occurence of MazEF-like Antitoxin/Toxin Systems in Bacteria", J. Mol. Microbiol. Biotechnol. (1999) 1(2): 295-302.
A. J. Munoz-Gomez et al., Insights into the specificity of RNA cleavage by the *Escherichia coli* MazF toxin, FEBS Letters (2004), 567: 316-320.
D. P. Pandey et al., "Toxin-antitoxin loci are highly abundant in free-living but lost from host-associated prokaryotes", Nucleic Acids Research (2005), 33(3): 966-976.
K. Pedersen et al., "The Bacterial Toxin RelE Displays Codon-Specific Cleavage of mRNAs in the Ribosomal A Site", Cell (2003), 112: 131-140.
H. Yoshida, "The Ribonuclease TI Family", Methods in Enzymology (2001), 341: 28-41.
J. Zhang et al., "Interference of mRNA Function by Sequence-specific Endoribonuclease PemK", J. of Biol. Chem. (2004), 279(20): 20678-20684.
Y. Zhang et al., "Insights into the mRNA Cleavage Mechanism by MazF, an mRNA Interferase", J. of Biol. Chem. (2005), 280(5): 3143-3150.
Y. Zhang et al., "MazF Cleaves Cellular mRNAs Specifically at ACA to Block Protein Synthesis in *Escherichia coli*", Molecular Cell (2003) 12: 913-923.
NCBI Sequence Viewer. Database DDBJ/EMBL/GenBank (online), Accession No. NC_001263; http://www.ncbi.nlm.nih.gov/entrez/viewer.fcgi?db=nucleotide&val=NC_001263. (Nucleotide), Sep. 26, 2001.
NCBI Sequence Viewer. Database DDBJ/EMBL/GenBank (online), Accession No. NP_294385; http://www.ncbi.nlm.nih.gov/entrez/viewer.fcgi?15805689:OLD10:220934 (Protein), Sep. 26, 2001.

* cited by examiner

*Primary Examiner* — Tekchand Saidha
*Assistant Examiner* — MD. Younus Meah
(74) *Attorney, Agent, or Firm* — Browdy and Neimark, PLLC

(57) ABSTRACT

A polypeptide having a endoribonuclease activity; a nucleic acid encoding the polypeptide; recombinant DNA having the nucleic acid therein; a transformant transformed with the recombinant DNA; a process for producing the polypeptide comprising the steps of cultivating the transformant and collecting the polypeptide from the culture; a process for producing a digest of single-stranded RNA comprising the step of reacting the polypeptide with the single-stranded RNA; and a method for the digestion of single-stranded RNA.

3 Claims, No Drawings

SEQUENCE LISTING

```
<160> NUMBER OF SEQ ID NOS: 14

<210> SEQ ID NO 1
<211> LENGTH: 115
<212> TYPE: PRT
<213> ORGANISM: Deinococcus radiodurans R1

<400> SEQUENCE: 1

Met Ala Val Gly Leu Ile Arg Arg Gly Asp Ile Phe Leu Thr His
  1               5                  10                  15

Phe Gly Pro Ala Arg Ala Gly Glu Pro Asp Phe Lys Arg Pro Ala
                 20                  25                  30

Val Val Ile Thr Asn Asn Val Ala Asn Ala Lys Ala Asp Ala Val
                 35                  40                  45

Thr Val Ile Pro Leu Thr Ser Asn Leu Glu Thr Leu Tyr Asp Phe
                 50                  55                  60

Gln Leu Leu Leu Pro Thr Glu Arg Thr Gly Leu Asn Leu Asp Ser
                 65                  70                  75
```

```
Lys Ala Gln Thr Glu Leu Ile Ser Cys Ile Ala Ile Ser Arg Ile
                80                  85                  90

Gly Lys His Leu Gly Gln Val Pro Ala Asp Leu Met Ala Glu Leu
            95                 100                 105

Asp Ala Arg Ile Arg Leu His Leu Ala Leu
            110                 115

<210> SEQ ID NO 2
<211> LENGTH: 114
<212> TYPE: PRT
<213> ORGANISM: Mycobacterium bovis BCG

<400> SEQUENCE: 2

Met Val Ile Ser Arg Ala Glu Ile Tyr Trp Ala Asp Leu Gly Pro
  1               5                  10                  15

Pro Ser Gly Ser Gln Pro Ala Lys Arg Arg Pro Val Leu Val Ile
                20                  25                  30

Gln Ser Asp Pro Tyr Asn Ala Ser Arg Leu Ala Thr Val Thr Ala
                35                  40                  45

Ala Val Ile Thr Ser Asn Thr Ala Leu Ala Ala Met Pro Gly Asn
                50                  55                  60

Val Phe Leu Pro Ala Thr Thr Thr Arg Leu Pro Arg Asp Ser Val
                65                  70                  75

Val Asn Val Thr Ala Ile Val Thr Leu Asn Lys Thr Asp Leu Thr
                80                  85                  90

Asp Arg Val Gly Glu Val Pro Ala Ser Leu Met His Glu Val Asp
                95                 100                 105

Arg Gly Leu Arg Arg Val Leu Asp Leu
                110

<210> SEQ ID NO 3
<211> LENGTH: 345
<212> TYPE: DNA
<213> ORGANISM: Deinococcus radiodurans R1

<400> SEQUENCE: 3
atggctgtag gactcatccg gcgcggcgac attttctga cccatttcgg ccccgcccgc      60
gcaggcgaac cggacttcaa cgccccgct gtggtcatca ccaacaatgt cgccaacgcc     120
aaagcggatg ccgtgaccgt cattccgctc accagcaacc tggaaaccct ctacgatttt     180
caactgctgc tccccaccga gcgaaccggg ctgaacttgg acagcaaagc gcagacggaa     240
ttgatctcgt gtattgccat cagccgcatc gggaagcacc tggggcaagt gccagccgac     300
ctcatggctg aactggacgc cagaatccgc cttcaccttg ccctg                    345

<210> SEQ ID NO 4
<211> LENGTH: 342
<212> TYPE: DNA
<213> ORGANISM: Mycobacterium bovis BCG

<400> SEQUENCE: 4
atggtgatta gtcgtgccga gatctactgg gctgacctcg gccgccatc aggcagtcag       60 ccggcgaagc gccgcccggt gctcgtaatc cagtcgatc cgtacaacgc aagtcgcctt     120
gccactgtga ccgcagcggt gatcacgtcc aatacggcgc tggcggcaat gcccggcaac     180
gtgttcttgc ccgcgaccac aacgcgactg ccacgtgact cggtcgtcaa cgtcacggcg     240
attgtcacgc tcaacaagac tgacctcacc gaccgagttg gggaggtgcc agcgagcttg     300
```

```
atgcacgagg ttgaccgagg acttcgtcgc gtactggacc tt                342
```

<210> SEQ ID NO 5
<211> LENGTH: 33
<212> TYPE: DNA
<213> ORGANISM: Artificial
<220> FEATURE:
<223> OTHER INFORMATION: PCR primer DR0662-F to amplify a DNA fragment
      encoding DR0662 protein.

<400> SEQUENCE: 5

```
ggggagctaa catatggctg taggactcat ccg                          33
```

<210> SEQ ID NO 6
<211> LENGTH: 28
<212> TYPE: DNA
<213> ORGANISM: Artificial
<220> FEATURE:
<223> OTHER INFORMATION: PCR primer DR0662-R to amplify a DNA fragment
      encoding DR0662 protein.

<400> SEQUENCE: 6

```
ggggctcgag cagggcaagg tgaaggcg                                28
```

<210> SEQ ID NO 7
<211> LENGTH: 365
<212> TYPE: DNA
<213> ORGANISM: Artificial
<220> FEATURE:
<223> OTHER INFORMATION: synthetic DNA encoding Mb2014c homolog protein.

<400> SEQUENCE: 7

```
ggggagctaa catatggtga ttagtcgtgc cgagatctac tgggctgacc tcgggccgcc    60
atcaggcagt cagccggcga agcgccgccc ggtgctcgta atccagtcag atccgtacaa   120
cgcaagtcgc cttgccactg tgaccgcagc ggtgatcacg tccaatacgg cgctggcggc   180
aatgcccggc aacgtgttct tgcccgcgac cacaacgcga ctgccacgtg actcggtcgt   240
caacgtcacg gcgattgtca cgctcaacaa gactgacctc accgaccgag ttggggaggt   300
gccagcgagc ttgatgcacg aggttgaccg aggacttcgt cgcgtactgg accttctcga   360
gcccc                                                              365
```

<210> SEQ ID NO 8
<211> LENGTH: 30
<212> TYPE: RNA
<213> ORGANISM: Artificial
<220> FEATURE:
<223> OTHER INFORMATION: Oligoribonucleotide MRI031.

<400> SEQUENCE: 8

```
guguguuccu uuauuugugu uacuuugggc                              30
```

<210> SEQ ID NO 9
<211> LENGTH: 28
<212> TYPE: RNA
<213> ORGANISM: Artificial
<220> FEATURE:
<223> OTHER INFORMATION: Oligoribonucleotide MRI019.

<400> SEQUENCE: 9

```
gggacucucu uccauccuua accggagg                                28
```

<210> SEQ ID NO 10
<211> LENGTH: 25
<212> TYPE: RNA

-continued

```
<213> ORGANISM: Artificial
<220> FEATURE:
<223> OTHER INFORMATION: Oligoribonucleotide MRI021.

<400> SEQUENCE: 10
gagucguggg cguacuuuau ggggc                                            25

<210> SEQ ID NO 11
<211> LENGTH: 30
<212> TYPE: RNA
<213> ORGANISM: Artificial
<220> FEATURE:
<223> OTHER INFORMATION: Oligoribonucleotide MRI023.

<400> SEQUENCE: 11
aucuacaggg aucuccuauc uacuaugggg                                       30

<210> SEQ ID NO 12
<211> LENGTH: 30
<212> TYPE: RNA
<213> ORGANISM: Artificial
<220> FEATURE:
<223> OTHER INFORMATION: Oligoribonucleotide MRI024.

<400> SEQUENCE: 12
auuuacaggg auuuccuauu uacuaugggg                                       30

<210> SEQ ID NO 13
<211> LENGTH: 30
<212> TYPE: RNA
<213> ORGANISM: Artificial
<220> FEATURE:
<223> OTHER INFORMATION: Oligoribonucleotide MRI025.

<400> SEQUENCE: 13
auauacaggg auauccuaua uacuaugggg                                       30

<210> SEQ ID NO 14
<211> LENGTH: 30
<212> TYPE: RNA
<213> ORGANISM: Artificial
<220> FEATURE:
<223> OTHER INFORMATION: Oligoribonucleotide MRI026.

<400> SEQUENCE: 14
auguacaggg auguccuaug uacuaugggg                                       30
```

ENDORIBONUCLEASE

TECHNICAL FIELD

The present invention relates to a novel sequence-specific endoribonuclease which is useful in the field of genetic engineering.

BACKGROUND ART

It has been reported that several prokaryotic plasmids have a post-segregation killing (PSK) function to kill hosts from which the plasmids have been dropped out in order to maintain the plasmids in the hosts. Such plasmids have toxin-antitoxin genes. An antitoxin binds to a toxin in a cell to inactivate the toxin. The antitoxin is labile to degradation by proteases. Degradation of the antitoxin by proteases results in activation of the toxin which is stable (Non-patent Document 1). Such toxin-antitoxin genes also exist on chromosomes of most prokaryotes. They respond to various stresses and have functions in programmed cell death. Although the functions of the toxins have not been fully proven, it has been suggested that CcdB and ParE may control replication targeting DNA gyrase, and RelE and Doc may control transcription (Non-patent Documents 1 and 2).

At least five toxins RelE, ChpAK (MazF), ChpBK, YoeB and YafQ exist in *Escherichia coli* (Non-patent Document 2). Christensen at al. have reported that RelE is an endoribonuclease that recognizes a specific codon of three nucleotides in a ribosome-dependent manner to cleave mRNA (Non-patent Documents 3 and 4). Furthermore, Christensen et al. have reported that ChpAK, ChpBK and YoeB are also endoribonucleases that cleave mRNA in a manner dependent on ribosome and codon (Non-patent Documents 5 and 6).

Inouye et al. have demonstrated that MazF (ChpAK) is an endoribonuclease that recognizes specific nucleotides ACA in a ribosome-independent manner to cleave mRNA (Non-patent Documents 7 and 8). Munoz-Gomez et al. have reported that the cleavage of RNA with mazF is specific for NAC (Non-patent Document 9). Inouye at al. have demonstrated that PemK in a plasmid R100 is an endoribonuclease that recognizes specific nucleotides UAH (H is C, A or U) to cleaves mRNA (Patent Document 1, Non-patent Document 10). As described above, it has been suggested that toxins of the RelE or PemK family may be endoribonucleases that cleave mRNA in a nucleotide-specific manner. In particular, toxins of the PemK family may be endoribonucleases that recognize specific nucleotides in a ribosome-independent manner to cleave mRNA. Many toxins of the PemK family exist in prokaryotes and comparison of their sequences has been studied extensively (Non-patent Documents 1 and 11).

Anantharaman et al, have phylogenetically classified toxins by conducting gene neighborhood analyses on the basis of genetic information about toxins and genetic information about organisms for which genomic analyses have been completed, and predicted toxin-like proteins from proteins of unknown functions (Non-patent Document 12). Furthermore, it has been suggested through the analyses that not only RelE and PemK but also proteins of the Doc family and proteins having PIN domains may have ribonuclease activities. Two toxins of the PemK family have been found in *Deinococcus radiodurans* (Non-patent Document 13). Seven toxins of the PemK family have been found in *Mycobacterium tuberculosis*. The same toxins exist in *Mycobacterium bovis*.

As to enzymes that cleave nucleic acids in a sequence-specific manner, many restriction enzymes which cleave double-stranded DNA have been found and widely utilized in the field of genetic engineering. As to enzymes that cleave single-stranded RNA in a sequence-specific manner, ribonuclease T1 which specifically cleaves at a G nucleotide has been found and utilized for genetic engineering (Non-patent Document 14). The number of enzymes that recognize plural nucleotides in single-stranded RNA and specifically cleave it is still small. Development of such endoribonucleases has been desired in the field of genetic engineering. If an endoribonuclease that specifically recognizes and cleaves a sequence of three nucleotides (like MazF) or more than three nucleotides is found, it is considered that the endoribonuclease would become a useful enzyme in the field of genetic engineering.

Patent Document 1: WO 2004/113498
Non-patent Document 1: J. Bacteriol., 182:561-572 (2000)
Non-patent Document 2: Science, 301:1496-1499 (2003)
Non-patent Document 3: Molecular Microbiol., 48:1389-1400 (2003)
Non-patent Document 4: Cell, 122:131-140 (2003)
Non-patent Document 5: J. Mol. Biol., 332:809-819 (2003)
Non-patent Document 6: Molecular Microbiol., 51:1705-1717 (2004)
Non-patent Document 7: Molecular Cell, 12:913-920 (2003)
Non-patent Document 8: J. Biol, Chem., 280:3143-3150 (2005)
Non-patent Document 9: FEBS Letters, 567:316-320 (2004)
Non-patent Document 10: J. Biol. Chem., 279:20678-20684 (2004)
Non-patent Document 11: J. Mol. Microbial. Biotechnol., 1:295-302 (1999)
Non-patent Document 12: Genome Biology, 4:R81 (2003)
Non-patent Document 13: Nucleic Acids Research, 33:966-976 (2005)
Non-patent Document 14: Methods in Enzymology, 341:28-41 (2001)

DISCLOSURE OF INVENTION

Problems to be Solved by the Invention

The present invention has been made in view of the above-mentioned prior art. The main object of the present invention is to find a novel sequence-specific endoribonuclease, to identify the cleavage sequence specificity of the novel sequence-specific endoribonuclease, and to provide its use for genetic engineering.

Means to Solve the Problems

The present inventors have screened for a sequence-specific endoribonuclease and found that polypeptides encoded by the genes for DR0662 in *Deinococcus radiodurans* and for Mb2014c homolog in *Mycobacterium bovis* BCG are novel sequence-specific endoribonucleases. Furthermore, the present inventors have identified the cleavage sequence specificities of the enzymes. Thus, the present invention has been completed.

The present invention relates to:

[1] a polypeptide having a sequence-specific endoribonuclease activity, which is represented by the amino acid sequence of SEQ ID NO:1 or 2 or an amino acid sequence in which one or more amino acid residue(s) is (are) deleted, added, inserted or substituted in said sequence;

[2] a nucleic acid encoding the polypeptide of [1];

[3] the nucleic acid of [2], which has the nucleotide sequence of SEQ ID NO:3 or 4;

[4] a nucleic acid that is capable of hybridizing to the nucleic acid of [2] or [3] under stringent conditions and encodes a polypeptide having a sequence-specific endoribonuclease activity;

[5] a recombinant DNA containing the nucleic acid of any one of [2] to [4];

[6] a transformant transformed with the recombinant DNA of [5];

[7] a method for producing the polypeptide of [1], the method comprising culturing the transformant of [6] and collecting a polypeptide having a sequence-specific RNA cleavage activity from the culture;

[8] a method for producing a single-stranded RNA degradation product, the method comprising allowing the polypeptide of [1] to act on a single-stranded RNA; and

[9] a method for degrading a single-stranded RNA, the method comprising allowing the polypeptide of [1] to act on a single-stranded RNA.

Effects of the Invention

The present invention enables finding of a novel sequence-specific endoribonuclease, identification of the cleavage sequence specificity of the novel sequence-specific endoribonuclease, and provision of its use for genetic engineering.

BEST MODE FOR CARRYING OUT THE INVENTION

1. The Polypeptide of the Present Invention

The polypeptide of the present invention is represented by the amino acid sequence of SEQ ID NO:1 or 2 or an amino acid sequence in which one or more amino acid residue(s) is (are) deleted, added, inserted or substituted in said amino acid sequence, and exhibits a sequence-specific endoribonuclease activity.

The activity possessed by the polypeptide of the present invention is an endoribonuclease activity specific for single-stranded RNA. The activity enables hydrolysis of a phosphodiester bond 3' to a ribonucleotide in a single-stranded nucleic acid containing the ribonucleotide as a constituting nucleotide. A nucleic acid hydrolyzed with the above-mentioned activity generates the following: a 3' end having a hydroxyl group and a 5' end having a phosphate group; a 3' end having a phosphate group and a 5' end having a hydroxyl group; or a 5' end having 2',3'-cyclic phosphate and a hydroxyl group.

A nucleic acid having at least one ribonucleotide molecule may be used as a substrate for the polypeptide of the present invention. Examples thereof include, but are not limited to, RNA, RNA containing deoxyribonucleotide(s) and DNA containing ribonucleotide(s). The substrate may contain a nucleotide that is different from ones contained in normal nucleic acids (e.g., deoxyinosine, deoxyuridine or hydroxymethyldeoxyuridine) as long as it does not inhibit the action of the polypeptide of the present invention.

The polypeptide of the present invention acts specifically on a single-stranded nucleic acid. It cannot cleave double-stranded nucleic acids such as a double-stranded RNA or an RNA-DNA hybrid.

The polypeptide of the present invention has an activity of cleaving a nucleic acid in a nucleotide sequence-specific manner. Although it is not intended to limit the present invention, for example, if a single-stranded RNA molecule contains a sequence 5'-UUCCUUU-3', a polypeptide having the amino acid sequence of SEQ ID NO:1 or SEQ ID NO:2 hydrolyzes a phosphodiester bond between the second U residue and the third C residue in the sequence. If a single-stranded RNA molecule contains a sequence 5'-UCCUU-3', a polypeptide having the amino acid sequence of SEQ ID NO:2 hydrolyzes a phosphodiester bond between the first U residue and the second C residue in the sequence. For example, the activity of the polypeptide can be confirmed using an oligoribonucleotide MRI031 (SEQ ID NO:8) as a substrate as an activity of hydrolyzing a phosphodiester bond between the 7th and 8th nucleotides in the oligoribonucleotide. The endoribonuclease activity of the polypeptide of the present invention is exhibited in the absence of ribosome. Thus, it is a ribosome-independent activity.

A single-stranded RNA-specific endoribonuclease activity of the polypeptide of the present invention can be measured, for example, using a single-stranded RNA as a substrate. Specifically, the measurement can be carried out by allowing a polypeptide to be subjected to activity measurement to act on a single-stranded RNA, which is transcribed from a DNA as a template using RNA polymerase or chemically synthesized, and determining the presence of RNA cleavage. For example, degradation of RNA can be confirmed using electrophoresis (agarose gel, acrylamide gel, etc.). Attachment of an appropriate label (e.g., radioisotope, fluorescent substance) to the RNA as a substrate facilitates detection of a degradation product following electrophoresis.

The polypeptides of the present invention include a polypeptide represented by an amino acid sequence in which one or more amino acid residue(s) is (are) deleted, added, inserted or substituted in the amino acid sequence of SEQ ID NO:1 or 2 as long as the polypeptide exhibits an endoribonuclease activity to hydrolyze single-stranded RNA in a sequence-specific manner. Examples of such mutant polypeptides include a polypeptide having 50% or more, preferably 70% or more, more preferably 90% or more homology to the polypeptide of SEQ ID NO:1 or 2. Such a mutant polypeptide is encompassed by the present invention even if it recognizes and cleaves a sequence different from the sequence recognized and cleaved by the polypeptide represented by the amino acid sequence of SEQ ID NO:1 or 2.

The polypeptide may have a peptide region that is not indispensable to the activity. For example, a polypeptide having the following being attached is included in the polypeptides of the present invention as long as the polypeptide exhibits a single-stranded RNA-specific RNA cleavage activity: a peptide for increasing translation efficiency; a peptide for facilitating purification of the polypeptide (e.g., histidine tag, glutathione-S-transferase, maltose binding protein); or a protein for increasing expression efficiency (e.g., chaperon).

2. The Nucleic Acid Encoding the Polypeptide of the Present Invention

The present invention provides a nucleic acid encoding a polypeptide having a sequence-specific endoribonuclease activity. Such nucleic acids include, but are not limited to, a nucleic acid encoding a polypeptide having a sequence-specific endoribonuclease activity, which is represented by the amino acid sequence of SEQ ID NO:1 or or an amino acid sequence in which one or more, for example one to ten amino acid residue(s) is (are) deleted, added, inserted or substituted in said sequence. Examples of amino acid sequences in which one or more amino acid residue(s) is (are) deleted, added, inserted or substituted in the amino acid sequence of SEQ ID NO:1 or 2 include an amino acid sequence having 50% or more, preferably 70% or more, more preferably 90% or more homology to the polypeptide of SEQ ID NO:1 or 2.

Furthermore, the nucleic acids of the present invention include a nucleic acid encoding a polypeptide having a sequence-specific endoribonuclease activity that is capable of hybridizing to such a nucleic acid under stringent conditions. The stringent conditions are exemplified by those described in J. Sambrook et al. (eds.), Molecular Cloning: A Laboratory Manual 2nd ed., 1989, Cold Spring Harbor Laboratory. Specifically, under exemplary conditions, incubation with a probe is conducted in 6×SSC containing 0.5% SDS, 5×Denhardt's solution, and 0.01% denatured salmon sperm DNA at 65° C. for 12 to 20 hours. For example, a nucleic acid hybridized with a probe can be detected after removing nonspecifically bound probes by washing in 0.1×SSC containing 0.5% SDS at 37° C.

For example, the nucleic acid encoding the polypeptide of the present invention can be obtained as follows.

A gene having a homology, in terms of the amino acid sequence, to a toxin having an endoribonuclease activity to recognize a specific nucleotide sequence and cleave mRNA (e.g., MazF or PemK) is a candidate for a nucleic acid encoding a polypeptide having a sequence-specific ribonuclease activity. For example, such a candidate gene can be found in a bacterial genome. Two toxins of the PemK family have been found in *Deinococcus radiodurans*. Seven toxins of the PemK family have been found in *Mycobacterium tuberculosis*. The same toxins exist in *Mycobacterium bovis*. Among the seven toxins, *Mycobacterium bovis* BOG has at least the homolog of Mb2014c (J. Bacterial, 178:1274-1282 (1996)).

For example, a candidate gene can be isolated from a bacterial genome by PCR using a primer designed based on nucleotide sequence information. If the entire nucleotide sequence is known, the entire sequence of the candidate gene may be synthesized using a DNA synthesizer.

A protein can be expressed from a candidate gene using an appropriate host (e.g., *Escherichia coli*) transformed with an expression vector having the candidate gene being incorporated. Since expression of a sequence-specific ribonuclease which degrades host RNA can be lethal to the host, it is necessary to strictly suppress the expression of the candidate gene before induction. For example, it is preferable to utilize an expression system such as the pET system (Novagen) which utilizes a promoter for T7 polymerase, or the pCold system (Takara Bio) which is a cold shock expression control system. For conveniently purifying an expression product from a candidate gene, it is advantageous to attach, to the expression product, a peptide for facilitating the purification (e.g., a histidine tag). For this purpose, one containing a region encoding such a peptide may be used as an expression vector.

An endoribonuclease activity can be measured according to the above-mentioned method in which a single-stranded RNA is used as a substrate. A cleavage site can be identified by primer extension using a cleaved RNA as a template, a primer complementary to the RNA and a reverse transcriptase. Since the extension reaction terminates at the cleavage site in the primer extension, the cleavage site can be identified by determining the chain length of the extended strand using electrophoresis. The nucleotide sequence specificity may be identified further strictly by chemically synthesizing oligoribonucleotides having arbitrary sequences, allowing the expression product of the candidate gene to act on them, and determining the presence of cleavage using denaturing acrylamide gel electrophoresis or the like.

3. The Method for Producing the Polypeptide of the Present Invention

For example, the polypeptide of the present invention can be produced by (1) purification from a culture of a microorganism producing the polypeptide of the present invention or (2) purification from a culture of a transformant containing a nucleic acid encoding the polypeptide of the present invention.

Examples of the microorganisms producing the polypeptide of the present invention include, but are not limited to, bacteria of the genus *Deinococcus* and the genus *Mycobacterium*. For example, the polypeptide of the present invention can be obtained from *D. radioduran* or *M. bovis*, preferably *D. radioduran* R1 or *M. bovis* BOG. The microorganism may be cultured under conditions suitable for the growth of the microorganism. The polypeptide of interest produced in the cells or the culture can be purified using a method conventionally used for protein purification such as cell disruption, fractionation by precipitation (e.g., ammonium sulfate precipitation), various chromatographies (ion exchange chromatography, affinity chromatography, hydrophobic chromatography, molecular sieve chromatography) or a combination thereof.

The polypeptide of the present invention can be obtained from a transformant transformed with a recombinant DNA containing a nucleic acid encoding the polypeptide of the present invention. Preferably, an appropriate promoter is operably linked upstream of a polypeptide-encoding nucleic acid in the recombinant DNA. Since the polypeptide of the present invention may exert a lethal action on a host, it is preferable that the promoter or an expression system including the promoter can strictly control the transcription from the nucleic acid encoding the polypeptide of the present invention. The pET system or the pCold system exemplifies such a system.

The recombinant DNA may be transferred as it is into a cell as a host. Alternatively, it may be transferred being inserted into an appropriate vector (e.g., a plasmid vector, a phage vector or a virus vector). The recombinant DNA may be integrated into the host chromosome. There is no specific limitation concerning the host to be transformed. For example, a host conventionally used in the field of recombinant DNA (e.g., *Escherichia coli*, *Bacillus subtilis*, yeast, filamentous fungus, plant, animal, plant culture cell, animal culture cell) may be used.

The polypeptide of the present invention produced from such a transformant can be purified utilizing the above-mentioned purification means. If the nucleic acid encoding the polypeptide of the present invention encodes a polypeptide having a peptide for facilitating purification of the polypeptide being attached, the purification is facilitated very much. A high purity polypeptide can be obtained according to a convenient procedure using a purification means corresponding to the attached peptide (e.g., metal chelate resin for histidine tag, glutathione-immobilized resin for glutathione-S-transferase).

4. Degradation of Single-Stranded RNA using the Polypeptide of the Present Invention An RNA degradation product can b produced by degrading a single-stranded RNA using the polypeptide of the present invention. Since the polypeptide of the present invention can cleave RNA in a nucleotide sequence-specific manner, the average chain length of the generated RNA degradation products is correlated with the occurrence frequency of the nucleotide sequence recognized by the polypeptide. Thus, the present invention provides an RNA degradation product having certain chain length distribution. Furthermore, it is possible to excise a specific region in RNA utilizing the sequence specificity.

Furthermore, it is possible to selectively degrade a single-stranded RNA using the polypeptide of the present invention. In one embodiment of the present invention, it is possible to inhibit protein synthesis by degrading mRNA in a protein synthesis system (e.g., a cell-free translation system or a transformant) using the polypeptide of the present invention. In this case, if mRNA encoding the protein of interest that has been artificially prepared not to contain a nucleotide sequence recognized by the polypeptide of the present invention is placed in the system, only the mRNA escapes from degradation and the protein of interest is specifically produced in the system. This embodiment is particularly useful for production of a highly pure protein.

EXAMPLES

The following Examples illustrate the present invention in more detail, but are not to be construed to limit the scope thereof.

Among the procedures described herein, basic procedures were carried out as described in J. Sambrook et al. (eds.), Molecular Cloning: A Laboratory Manual 3rd ed., 2001, Cold Spring Harbor Laboratory.

Example 1

Isolation of DR0662 from *D. radioduran* R1 and Mb2014c Homolog from *M. bovis* BCG, and Construction of Expression Plasmids Amino acid sequences of polypeptides encoded in *Deinococcus radioduran* R1-derived DR0662 gene and *Mycobacterium bovis* BCG-derived Mb2014c homolog gene as well as the nucleotide sequences therefor were obtained from NCBI database (accession nos. NP_294385 and NC_001263, and NP_855664 and NC_002945). A primer DR0662-F (SEQ ID NO:5) and a primer DR0062-R (SEQ ID NO:6) were synthesized for PCR amplification of a DNA region encoding the entire polypeptide based on the information about the nucleotide sequence of DR0662.

*Deinococcus radioduran* R1 genomic DNA was obtained from ATCC (ATCC No. 13939D). PCR was conducted using Pyrobest DNA polymerase (Takara Bio) as well as 50 ng of the genomic DNA from *Deinococcus radioduran* R1 and the primers DR0662-F and DR0662-R to obtain a 368-bp amplified DNA fragment. The amplified fragment was digested with restriction enzymes NdeI and XhoI and subjected to agarose gel electrophoresis, and a 347-bp DNA fragment was recovered from the gel. As to Mb2014c homolog from *Mycobacterium bovis* BCG, a 365-bp dsDNA of SEQ ID NO:7 was chemically synthesized and digested with NdeI and XhoI to obtain a 344-bp restriction enzyme-digested DNA fragment. Recombinant plasmids were obtained by ligating the 347-bp DNA fragment or the 344-bp DNA fragment to a vector pET21a (Novagen) which had been digested with restriction enzymes NdeI and XhoI. These recombinant plasmids were used to transform *Escherichia coli* JM109. Plasmids were prepared from colonies of transformants obtained as described above and the nucleotide sequences were confirmed. Then, the plasmids were designated as expression vectors pET-DR0662 and pET-Mb2014cHlg, respectively.

The nucleotide sequence encoding the *Deinococcus radioduran* R1-derived DR0662 polypeptide inserted in the thus obtained expression vector pET-DR0662 and the amino acid sequence of the polypeptide are shown in SEQ ID NOS:3 and 1, respectively. The nucleotide sequence encoding the *Mycobacterium bovis* BCG-derived Mb2014c homolog polypeptide inserted in the expression vector pET-Mb2014cHlg and the amino acid sequence of the polypeptide are shown in SEQ ID NOS:4 and 2, respectively. In each of the polypeptides expressed using the expression vectors pET-DR0662 and pET-Mb2014cHlg, a histidine tag that consists of eight amino acid residues including six histidine residues is attached at the C terminus of the polypeptide of the amino acid sequence of SEQ ID NO:1 or 2.

Example 2

Preparation of *D. radioduran* R1-Derived DR0662 Polypeptide and *M. bovis* BCG-Derived Mb2014c Homolog Polypeptide The expression vector pET-DR0662 or pET-Mb2014cHlg obtained in Example 1 was used to transform *Escherichia coli* BL21(DE3) (Novagen) to obtain *Escherichia coli* for expression, pET-DR0662/BL21(DE3) and pET-Mb2014cHlg/BL21 (DE3). pET-DR0662/BL21(DE3) or pET-Mb2014cHlg/BL21(DE3) was cultured in 5 ml of LB medium containing 100 μg/ml of ampicillin at 37° C. When OD600 nm reached 0.6, IPTG (Takara Bio) was added at a final concentration of 1 mM to induce expression of the polypeptide. The cultivation was terminated two hours after the initiation of induction, and the cells were collected by centrifugation. The cells were suspended in 300 μl of a lysis buffer (50 mM NaH$_2$PO$_4$, 300 mM NaCl, 10 mM imidazole, pH 8.0), and disrupted using a sonicator (Handy sonic, Tomy). 20 μl of Ni-NTA agarose (Qiagen) was added to a supernatant collected by centrifugation, and the mixture was allowed to stand at 4° C. for 30 minutes. A precipitate collected by centrifugation was washed twice with 100 μl of a washing buffer (50 mM NaH$_2$PO$_4$, 300 mM NaCl, 20 mM imidazole, pH 8.0). After washing, the precipitate was suspended in 20 μl of an elution buffer (50 mM NaH$_2$PO$_4$, 300 mM NaCl, 250 mM imidazole, pH 8.0). A supernatant was collected by centrifugation. The same elution procedure was repeated two more times. A total of 60 μl each of samples containing the DR0662 polypeptide or the Mb2014c homolog polypeptide was obtained. Portions of the samples were subjected to SDS-PAGE to confirm that the samples contained polypeptides of the expected sizes The concentrations of the DR0662 protein and the Mb2014c homolog protein in the samples were about 25 ng/μl and about 6.25 ng/μl, respectively.

Example 3

Identification of Nucleotide Sequence Specificities of DR0662 Polypeptide and Mb2014c Homolog Polypeptide using Oligoribonucleotides as Substrates Oligoribonucleotides were synthesized and cleavage assays were carried out in order to study the nucleotide sequence specificities of ribonuclease activities of the DR0662 polypeptide and the Mb2014c homolog polypeptide obtained in Example 2.

Seven oligoribonucleotides of SEQ ID NOS:8-14 were synthesized as substrates. A 5-μl reaction mixture consisting of 10 μM of one of the oligoribonucleotides, 2.5 ng/μl of the DR0662 polypeptide or the Mb2014c homolog polypeptide obtained in Example 2 and 10 mM Tris-HCl (pH 7.5) was incubated at 37° C. for 30 minutes. The reaction product was subjected to electrophoresis on 20% denaturing acrylamide gel (20% acrylamide, 7 M urea, 0.5×TBE buffer). After staining with SYBR GREEN II (Takara Bio), the fluorescence image was analyzed using a fluorescence image analyzer FMBIO II Multiview (Takara Bio). Cleavage modes of the respective oligoribonucleotides are shown in Table 1.

The cleavage modes are indicated as follows: +++: complete cleavage; ++: partial cleavage; +: very little cleavage; and −: complete lack of degradation. Furthermore, the sequence specificity was estimated by comparison of nucleotide sequences surrounding the cleavage sites in view of the presence or the degree of cleavage of each oligoribonucleotide. The results are shown in Table 2.

Based on the results, it was shown that the DR0662 polypeptide preferentially recognize a sequence 5'-UU/CCUUU-3' (/represents the cleavage site) to cleave RNA. Furthermore, it was shown that the Mb2014c homolog polypeptide preferentially recognize a sequence 5'-U/CCUU-3' to cleave RNA. It has been reported that MazF cleaves 5'-N/ACA-3' (N represents an arbitrary ribonucleotide) (Non-patent Documents 7 and 8). It was shown that the DR0662 polypeptide and the Mb2014c homolog polypeptide are endoribonucleases each having nucleotide sequence specificity quite different from that of MazF.

TABLE 1

| Name | Nucleotide sequence and cleavage site (/ represents cleavage site) | Degree of cleavage DR0662 | Mb2014c homolog |
|---|---|---|---|
| MRI031 | GUGUGUU / CCUUUAUUUGUGUUACUUUGGGC | +− | ++ |
| MRI019 | GGGACUCUCUUCCAU / CCUUAACCGGAGG | − | ++ |
| MRI021 | GAGUCGUGGGCGU / ACUUUAUGGGC | + | + |
| MRI023 | AUCUACAGGGAUCU / CCUAUCUACUAUGGGG | − | + |
| MRI024 | AUUUACAGGGAUUU / CCUAUUUACUAUGGGG | − | + |
| MRI025 | AUAUACAGGGAUAUCCUAUAUACUAUGGGG | − | − |
| MRI026 | AUGUACAGGGAUGUCCUAUGUACUAUGGGG | − | − |

Indication of cleavage: +++: complete cleavage; ++: partial cleavage, +: very little cleavage.

TABLE 2

| Name | Nucleotide sequence | | | | | | | Degree of cleavage | |
|---|---|---|---|---|---|---|---|---|---|
| | −2 | −1 | 1 | 2 | 3 | 4 | 5 | DR0662 | Mb2014c homolog |
| MRI031 | U | U | C | C | U | U | U | ++ | ++ |
| MRI019 | A | U | C | C | U | U | A | − | ++ |
| MRI021 | G | U | A | C | U | U | U | + | + |
| MRI023 | C | U | C | C | U | A | U | − | + |
| MRI024 | U | U | C | C | U | A | U | − | + |
| MRI025 | A | U | C | C | U | A | U | − | − |
| MRI026 | G | U | C | C | U | A | U | − | − |

Cleavage site: cleaved at a site berween −1 and +1.

INDUSTRIAL APPLICABILITY

The present invention provides a novel sequence-specific endoribonuclease. Since the enzyme can recognize and cleave a specific sequence in RNA, it is useful for analysis of RNA molecules, preparation of RNA fragments, control of cells (e.g., inhibition of protein synthesis) through cleavage of intracellular RNA, and the like.

SEQUENCE LISTING FREE TEXT

SEQ ID NO:5; PCR primer DR0662-F to amplify a DNA fragment encoding DR0662 protein.
SEQ ID NO:6; PCR primer DR0662-R to amplify a DNA fragment encoding DR0662 protein.
SEQ ID NO:7; synthetic DNA encoding Mb2014c homolog protein.
SEQ ID NO:8; Oligoribonucleotide MRI031.
SEQ ID NO:9; Oligoribonucleotide MRI019.
SEQ ID NO:10; Oligoribonucleotide MRI021.
SEQ ID NO:11; Oligoribonucleotide MRI023.
SEQ ID NO:12; Oligoribonucleotide MRI024.
SEQ ID NO:13; Oligoribonucleotide MRI025.
SEQ ID NO:14; Oligoribonucleotide MRI026.

The invention claimed is:

1. A method for producing a single-stranded RNA degradation product, the method comprising allowing a polypeptide having a sequence-specific endoribonuclease activity to act on a single-stranded RNA, wherein the polypeptide comprises the amino acid sequence of SEQ ID NO:1.

2. A method for degrading a single-stranded RNA, the method comprising allowing a polypeptide having a sequence-specific endoribonuclease activity to act on a single-stranded RNA, wherein the polypeptide comprises the amino acid sequence of SEQ ID NO:1.

3. The method of claim 2, wherein the polypeptide degrades mRNA in a protein synthesis system and inhibits protein synthesis.

* * * * *